United States Patent [19]

Serini et al.

[11] Patent Number: 5,212,280

[45] Date of Patent: May 18, 1993

[54] POLYCARBONATE FROM SPECIAL DIHYDROXYDIPHENYL BICYCLOALKANE

[75] Inventors: Volker Serini, Krefeld; Uwe Westeppe, Mettmann; Gerd Fengler, Krefeld-Traar; Manfred Hajek, Leverkusen; Carl Casser, Koeln; Helmut Waldmann, Leverkusen, all of Fed. Rep. of Germany

[73] Assignee: Bayer Aktiengesellschaft, Leverkusen, Fed. Rep. of Germany

[21] Appl. No.: 767,729

[22] Filed: Sep. 30, 1991

[30] Foreign Application Priority Data

Oct. 6, 1990 [DE] Fed. Rep. of Germany ....... 4031756

[51] Int. Cl.⁵ .............................................. C08G 64/04
[52] U.S. Cl. .................... 528/201; 528/125; 528/171; 528/174; 528/196; 528/204
[58] Field of Search ............... 528/201, 204, 125, 171, 528/174, 196

[56] References Cited

U.S. PATENT DOCUMENTS

| | | | |
|---|---|---|---|
| 3,879,347 | 4/1975 | Serini et al. | 260/47 XA |
| 3,879,348 | 4/1975 | Serini et al. | 260/47 XA |
| 4,277,600 | 7/1981 | Mark et al. | 528/204 |
| 4,301,311 | 11/1981 | Müller et al. | 568/719 |
| 4,446,298 | 5/1984 | Mark et al. | 528/204 |
| 4,520,187 | 5/1985 | Mark et al. | 528/176 |
| 4,554,309 | 11/1985 | Mark et al. | 524/611 |
| 4,576,996 | 3/1986 | Mark et al. | 525/439 |
| 4,663,434 | 5/1987 | Mark et al. | 568/640 |
| 4,675,458 | 6/1987 | Riemann et al. | 568/727 |
| 4,982,014 | 1/1991 | Freitag et al. | 568/721 |

FOREIGN PATENT DOCUMENTS 8000348 3/1980 World Int. Prop. O. .

OTHER PUBLICATIONS

Patent Abstracts of Japan No. 1-157926, vol. 13, No. 419, Sep. 18, 1989.

*Primary Examiner*—Harold D. Anderson
*Attorney, Agent, or Firm*—Joseph C. Gil; Aron Preis

[57] ABSTRACT

Dihydroxydiphenyl bicycloalkanes characterized in that they contain 9 to 13 ring C atoms in the bicycloaliphatic component are disclosed. The disclosed compounds were found to be suitable for the preparation of high molecular weight, thermoplastic polycarbonate resins having favorable properties.

4 Claims, No Drawings

POLYCARBONATE FROM SPECIAL DIHYDROXYDIPHENYL BICYCLOALKANE

This invention relates to dihydroxydiphenyl bicycloalkanes corresponding to formula (I)

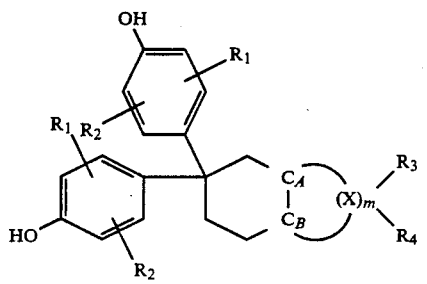

in which

R$_1$ and R$_2$ independently of one another represent hydrogen, halogen, preferably chlorine or bromine, C$_{1-8}$ alkyl, C$_{5-6}$ cycloalkyl, C$_{6-10}$ preferably phenyl, and C$_{7-12}$ aralkyl, preferably phenyl-C$_{1-4}$-alkyl, more particularly benzyl, m is an integer of from 3 to 7, preferably 3 or 4, R$_3$ and R$_4$ are individually selected for each X and, independently of one another represent, hydrogen, linear or branched C$_{1-6}$ alkyl, C$_{6-10}$ aryl, preferably phenyl, or aralkyl and x represents carbon, with the proviso that, at at least one atom X, R$_3$ and R$_4$ are not both hydrogen.

R$_3$ and R$_4$ are both alkyl at preferably 1 to 2 atoms X, but more especially at two atoms X. The preferred alkyl radical is methyl. The X atoms in the alpha position to the two bridge C atoms (C$_A$ and C$_B$) are preferably dialkyl-substituted. More preferably, one X atom in alpha position to C$_A$ or C$_B$ is mono-or dialkyl-substituted.

More particularly, the invention relates to dihydroxydiphenyl bicycloalkanes containing 9 and 10 ring C atoms in the bicycloaliphatic component (m=3 or 4 in formula (I)), for example diphenols corresponding to the following formulae

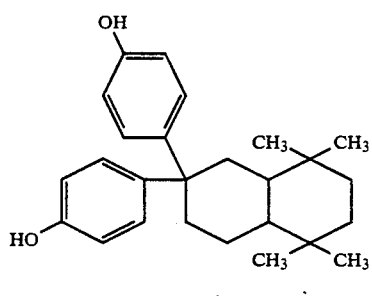

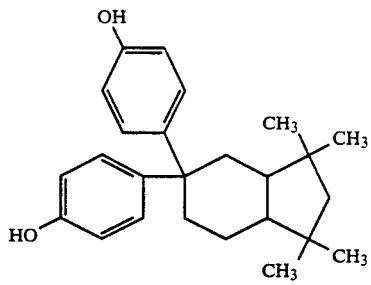

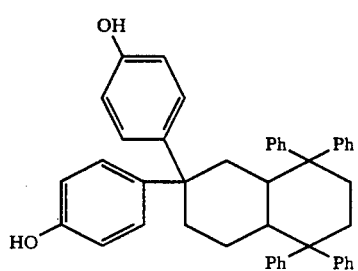

(Ph = phenyl)

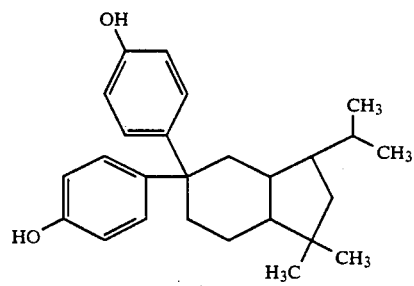

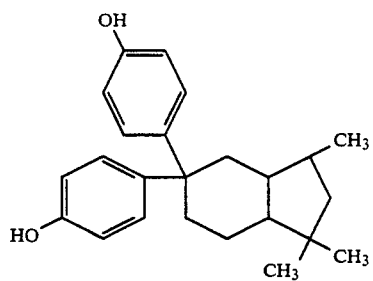

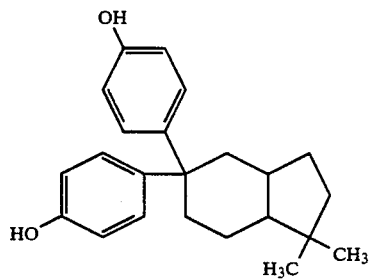

The dihydroxydiphenyl bicycloalkanes corresponding to formula (I) may be obtained in known manner by condensation of phenols corresponding to formula (VIII)

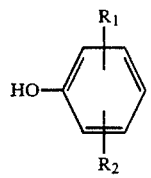 (VIII)

and ketones corresponding to formula (IX)

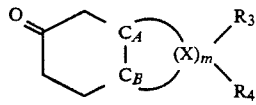 (IX)

in formulae (VIII) and (IX), X, $R_1$, $R_2$, $R_3$, $R_4$ and m are as defined for formula (I).

The phenols corresponding to formula (VIII) are either known from the literature or may be obtained by methods known from the literature (for cresols and xylenols, see for example Ullmanns Encyklopädie der technischen Chemie, 4th Revised and Extended edition, Vol. 15, pages 61-77, Verlag Chemie, Weinheim/New York, 1978; for chlorophenols, Ullmanns Encyklopädie der technischen Chemie, 4th Edition, Verlag Chemie, 1975, Vol. 9, pages 573-582; and for alkylphenols, Ullmanns Encyklopädie der technischen Chemie, 4th Edition, Verlag Chemie 1979, Vol. 18, pages 191-214).

Examples of suitable phenols corresponding to formula (VIII) are phenol, o-cresol, m-cresol, 2,6-dimethylphenol, 2-chlorophenol, 3-chlorophenol, 2,6-dichlorophenol, 2-cyclohexylphenol, diphenylphenol and o-benzylphenol.

The ketones corresponding to formula (IX) may be obtained from the phenols (X) known from the literature (cf. for example Houben-Weyl, Methoden der organischen Chemie, Vol. VI/1c, G. Thieme Verlag Stuttgart, 1976 pages 925-1022)

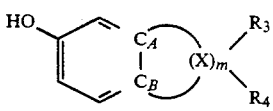 (X)

in which $R_3$, $R_4$, X and m are as defined above, by the generally known reaction sequence hydrogenation of the aromatic ring to the secondary alcohol and subsequent oxidation to the ketone. Direct hydrogenation of the phenols corresponding to formula (X) to the ketones corresponding to formula (IX) is also possible (see Houben-Weyl, Methoden der organischen Chemie, 4th Edition, Vol. 4/1c, pages 177-188, G. Thieme Verlag Stuttgart, 1980).

The following are examples of suitable ketones corresponding to formula (IX):

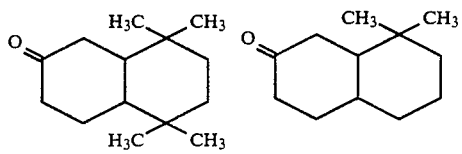

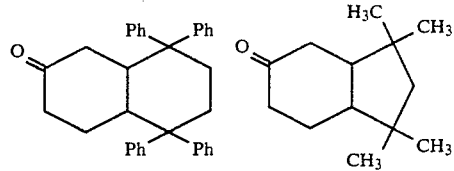

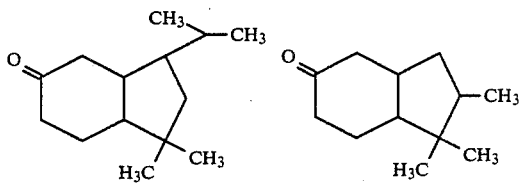

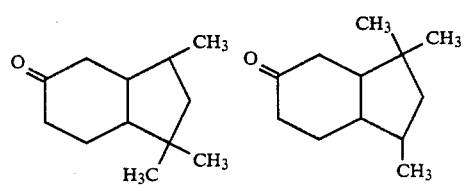

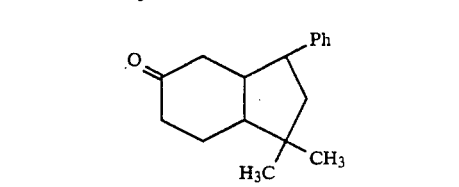

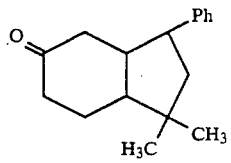

To prepare the bisphenols, the phenol (VIII) is generally used in a quantity of 2 to 30 mol and preferably in a quantity of 2.5 to 20 mol per mol ketone (IX). Preferred reaction times are from 1 to 300 hours. The reaction is generally carried out at a temperature in the range from $-30°$ C. to $300°$ C. and preferably at a temperature in the range from $-15°$ C. to $150°$ C. and under a pressure of from 1 to 20 bar and preferably under a pressure of from 1 to 10 bar.

The condensation is generally carried out in the presence of acidic catalysts such as, for example, hydrogen chloride, hydrogen bromide, hydrogen fluoride, boron trifluoride, aluminium trichloride, zinc dichloride, titanium tetrachloride, tin tetrachloride, phosphorus halides, phosphorus pentoxide, phosphoric acid, concentrated hydrochloric acid or sulfuric acid, aromatic or aliphatic sulfonic acids, mixtures of acetic acid and acetanhydride and aromatic or aliphatic sulfonic acids. Acidic ion exchangers, acidic zeolites or trimethyl chlorosilane may also be used.

In addition, the reaction may be accelerated by addition of co-catalysts, such as $C_1$-$C_{18}$ alkyl mercaptans, hydrogen sulfide, thiophenols, thio acids and dialkyl sulfides in quantities of 0.001 to 0.4 mol/mol ketone and more particularly in quantities of 0.01 to 0.2 mol/mol ketone.

In cases where the catalyst also acts as a dehydrating agent, there is no need to use separate dehydrating agents, although, to obtain good conversions, it is always of advantage to use dehydrating agents when the catalyst used does not bind the water of reaction.

Suitable dehydrating agents are, for example, acetanhydride, zeolites, polyphosphoric acid and phosphorus pentoxide.

The condensation may be carried out in the absence of solvents or in the presence of an inert solvent (for example aliphatic and aromatic hydrocarbons, chlorinated hydrocarbons).

In some cases, the reaction is not entirely uniform, i.e. several different products can be formed, so that the desired compound first has to be isolated from a mixture. For particulars of the condensation, reference may be made to Schnell, Chemistry and Physics of Polycarbonates, Interscience Publishers, New York 1964. In some cases, it is possible to control the reaction through the choice of suitable catalysts and reaction conditions in such a way that the desired compound precipitates or crystallizes out, which makes it easier to isolate.

Accordingly, the present invention also relates to a process for the production of the dihydroxydiphenyl bicycloalkanes corresponding to formula (I)

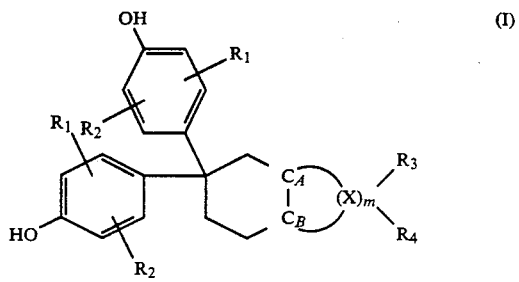

(I)

in which $R_1$ and $R_2$ independently of one another represent hydrogen, halogen, preferably chlorine or bromine, $C_{1-8}$ alkyl, $C_{5-6}$ cycloalkyl, $C_{6-10}$ aryl, preferably phenyl, and $C_{7-12}$ aralkyl, preferably phenyl-$C_{1-4}$-alkyl, more particularly benzyl, is an integer of from 3 to 7, preferably 3 or 4, $R_3$ and $R_4$ are individually selected for each X and, independently of one another represent, hydrogen, linear or branched $C_{1-6}$ alkyl, $C_{6-10}$ aryl, preferably phenyl, or aralkyl and represents carbon, with the proviso that, at at least one atom X, $R_3$ and $R_4$ are not both hydrogen, characterized in that phenols corresponding to formula (VIII)

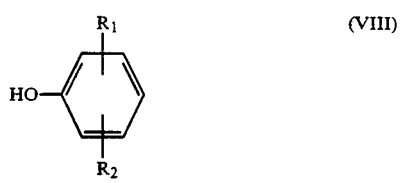

(VIII)

are reacted with ketones corresponding to formula (IX)

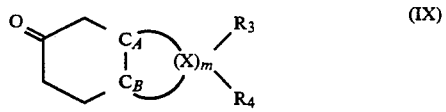

(IX)

in which

X, m, $R_1$, $R_2$, $R_3$ and $R_4$ are as defined for formula (I), in a molar ratio of (VIII):(IX) of from 2:1 to 30:1 and preferably in a molar ratio of from 2.5:1 to 20:1 at temperatures in the range from −30° C. to 300° C. and preferably at temperatures in the range from −15° to 150° C. and under pressures of from 1 to 20 bar and preferably 1 to 10 bar in the presence of acidic catalysts and optionally in the presence of co-catalysts and/or solvents and/or dehydrating agents.

$R_3$ and $R_4$ are both alkyl at preferably 1 to 2 atoms X, but more especially at two atoms X. The preferred alkyl radical is methyl. The X atoms in the a-position to the two bridge C atoms ($C_A$ and $C_B$) are preferably dialkyl-substituted. More preferably, one X atom in the a-position to $C_A$ or $C_B$ is mono- or dialkyl-substituted.

Preparation of the dihydroxydiphenyl bicycloalkanes

The structure of the dihydroxydiphenyl bicycloalkanes according to the invention is in accordance with the results of $^1$H-NMR and mass spectroscopy.

EXAMPLE A.1

Preparation of the diphenol 1,1,4,4-tetramethyl-7,7-bis-(4-hydroxyphenyl)-decalin (II)

282 g (3 mol) phenol, 104 g (0.5 mol) 1,1,4,4-tetramethyl decalin-7-one and 10.1 g (0.05 mol) dodecylthiol are introduced at 26° C. into a stirred reactor equipped with a stirrer, thermometer and reflux condenser. 30 g 37% HCl are then added to the solution. The reaction mixture is stirred at 20° to 35° C. until a 95% conversion has been obtained. The reaction mixture is then repeatedly extracted with water. The resulting phenol-bisphenol adduct is substantially freed from phenol and secondary products by repeated washing with hexane and subsequently recrystallized from toluene. Yield: 153 g. Melting point: 188° to 191° C.

EXAMPLE A.2

Preparation of the diphenol 1,1,4,4-tetramethyl-7,7-bis-(3,5-dimethyl-4-hydroxyphenyl)-decalin The procedure was as in Example 1 except that 3 mol 2,6-dimethylphenol were used instead of 3 mol phenol and the reaction was carried out at 40° C. Melting point: 229° to 234° C.

EXAMPLE A.3

Preparation of the diphenol 1,1,3,3-tetramethyl-5,5-bis-(4-hydroxyphenyl)-indane (III)

The procedure was as in Example 1 except that 0.5 mol 1,1,3,3-tetramethylindan-5-one was used instead of 0.5 mol 1,1,4,4-tetramethyldecalin-7-one. Melting point: 208° to 209° C.

The diphenols of formula (I) according to the invention are particularly suitable for the production of high molecular weight, thermoplastic polycarbonates which are distinguished by favorable properties.

Accordingly, the present invention also relates to the use of the diphenols of formula (I) for the production of high molecular weight thermoplastic, aromatic polycarbonates.

It is possible to use both a single diphenol corresponding to formula (I), in which case homopolycarbonates are formed, and also several diphenols corresponding to formula (I), in which case copolycarbonates are formed.

In addition, the diphenols corresponding to formula (I) may also be used in admixture with other diphenols, for example with those corresponding to the formula HO—Z—OH (IX), for the production of high molecular weight, thermoplastic aromatic polycarbonates.

Suitable other diphenols corresponding to the formula HO—Z—OH (XI) are those in which Z is an aromatic radical containing 6 to 30 C. atoms which may contain one or more aromatic nuclei, may be substituted and may contain aliphatic radicals or other cycloaliphatic radicals than those corresponding to formula (I) or heteroatoms as bridge members.

Examples of diphenols corresponding to formula (XI) are hydroquinone, resorcinol, dihydroxydiphenyls, bis-hydroxyphenyl)-alkanes, bis-(hydroxyphenyl)cycloalkanes, bis-(hydroxyphenyl)-sulfides, bis-(hydroxyphenyl)-ethers, bis-(hydroxyphenyl)-ketones, bis-(hydroxyphenyl)-sulfones, bis-(hydroxyphenyl)sulfoxides, a,a'-bis-(hydroxyphenyl)- diisopropylbenzenes and nucleus-alkylated and nucleus-halogenated compounds thereof.

These and other suitable other diphenols are described, for example, in U.S. Pat. Nos. 3,028,365, 2,999,835, 3,148,172, 3,275,601, 2,991,273, 3,271,367, 3,062,781, 2,970,131 and 2,999,846; in DE-OSS 1,570,703, 2,063,050, 2,063,052, 2,211,056, 3,832,396, in FR-PS 1 561 518 and in the book by H. Schnell entitled "Chemistry and Physics of Polycarbonates", Interscience Publishers, New York, 1964.

Preferred other diphenols are, for example, 4,4'-dihydroxydiphenyl, 2,2-bis(4-hydroxyphenyl)-propane, 2,4-bis-(4-hydroxyphenyl)-2-methylbutane, 1,1-bis(4-hydroxyphenyl)-cyclohexane, a,a'-bis-(4-hydroxyphenyl)-p-diisopropylbenzene, 2,2-bis-(3-methyl-4-hydroxyphenyl)-propane, 2,2-bis-(3-chloro-4-hydroxyphenyl)propane, bis-(3,5-dimethyl-4-hydroxyphenyl)-methane, 2,2-bis-(3,5-dimethyl-4hydroxyphenyl)-propane, bis-(3,5-dimethyl-4-hydroxyphenyl)-sulfone, 2,4-bis-(3,5-dimethyl-4-hydroxyphenyl)-2-methylbutane, 1,1-bis-(3,5-dimethyl-4-hydroxyphenyl)-cyclohexane, 1,1-bis-(4-hydroxyphenyl)-3,3,5-trimethyl cyclohexane, a,a'-bis-(3,5-dimethyl-4-hydroxyphenyl)-p-diisopropylbenzene, 2,2-bis(3,5-dichloro-4-hydroxyphenyl)-propane and 2,2-bis-(3,5-dibromo-4-hydroxyphenyl)-propane.

Particularly preferred diphenols corresponding to formula (XI) are, for example, 2,2-bis-(4-hydroxyphenyl)-propane, 2,2-bis-(3,5-dimethyl-4-hydroxyphenyl)-propane, 2,2-bis-(3,5-dichloro-4-hydroxyphenyl)-propane, 2,2-bis(3,5-dibromo-4-hydroxyphenyl)-propane and 1,1-bis-(4-hydroxyphenyl)cyclohexane.

2,2-Bis-(4-hydroxyphenyl)-propane is particularly preferred.

The other diphenols may be used both individually and in admixture with one another.

The molar ratio of diphenols corresponding to formula (I) to be used in accordance with the invention to the other diphenols optionally used, for example those corresponding to formula (XI), should be between 100 mol-% (I) to 0 mol-% other diphenol and 2 mol-% (I) to 98 mol-% other diphenol, preferably between 100 mol-% (I) to 0 mol-% other diphenol and 5 mol-% (I) to 95 mol-% other diphenol and, more preferably, between 100 mol-% (I) to 0 mol-% other diphenol and 10 mol-% (I) to 90 mol-% other diphenol and, most preferably, between 100 mol-% (I) to 0 mol-% other diphenol and 20 mol-% (I) to 80 mol-% other diphenol.

The high molecular weight polycarbonates of the diphenols corresponding to formula (I), optionally in combination with other diphenols, may be prepared by any of the known methods used to produce polycarbonates. The various diphenols may be attached to one another both statistically and also in blocks.

Accordingly, the present invention also relates to a process for the production of high molecular weight, thermoplastic aromatic polycarbonates from diphenols, optionally chain terminators and optionally branching agents by the known methods for the production of polycarbonates, preferably by the interfacial process, characterized in that diphenols of formula (I) are used as the diphenols in quantities of from 100 mol-% to 2 mol-%, preferably in quantities of from 100 mol-% to 5 mol-%, more preferably in quantities of from 100 mol-% to 10 mol-% and most preferably in quantities of from 100 mol-% to 20 mol-%, based on the total mols diphenols used.

Monofunctional compounds in the usual concentrations are used in known manner as chain terminators for regulating molecular weight. Suitable compounds are, for example, phenol, tert.-butylphenols or other alkyl-$C_1$-$C_7$-substituted phenols.

Small quantities of phenols corresponding to formula (XII)

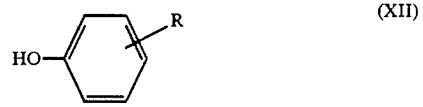

in which R is a branched $C_8$ and/or $C_9$ alkyl radical, are particularly suitable for regulating molecular weight. In the alkyl radical R, the percentage of $CH_3$ protons is between 47 and 89% and the percentage of CH and $CH_2$ protons between 53 and 11%. R is preferably in the o- and/or p-position to the OH group, 20% being the particularly preferred upper limit to the ortho component. The chain terminators are generally used in quantities of from 0.5 to 10 mol-% and preferably in quantities of from 1.5 to 8 mol-%, based on the diphenols used.

The branching agents if any, used to obtain branched polycarbonates are-in known manner-small quantities, preferably of from 0.05 to 2.0 mol-% (based on diphenols used), of trifunctional or more than trifunctional compounds, particularly those containing three or more than three phenolic hydroxyl groups. Some of the compounds containing three or more than three phenolic hydroxyl groups which may be used include phloroglucinol, 4,6-dimethyl-2,4,6-tri-(4-hydroxyphenyl)-hept-2-ene, 4,6-dimethyl-2,4,6-tri-(4-hydroxyphenyl)-heptane, 1,3,5-tri-(4-hydroxyphenyl)-benzene, 1,1,1-tri-(4-hydroxyphenyl)-ethane, tri-(4-hydroxyphenyl)-phenylmethane, 2,2-bis-(4,4-bis-(4-hydroxyphenyl)-cyclohexyl)propane, 2,4-bis-(4-hydroxyphenylisopropyl)-phenol, 2,6-bis-(2-hydroxy-5-methylbenzyl)-4-methylphenol, 2-(4-hydroxyphenyl)-2-(2,4-dihydroxyphenyl)propane, hexa-(4-(4-hydroxyphenylisopropyl)-phenyl)-orthoterephthalic acid ester, tetra-(4-hydroxyphenyl)-methane, tetra-(4-(4-hydroxyphenylisopropyl)-phenoxy)methane and 1,4-bis-((4',4"-dihydroxytriphenyl)-methyl)-benzene.

Some of the other trifunctional compounds are 2,4-dihydroxybenzoic acid, trimesic acid, cyanuric chloride and 3,3-bis-(3-methyl-4-hydroxyphenyl)-2-oxo-2,3-dihydroindole.

The polycarbonates according to the invention may be produced in known manner, preferably by the interfacial process (cf. H. Schnell "Chemistry and Physics of Polycarbonates", Polymer Reviews, Vol. IX, pages 33 et seq, Interscience Publ., 1964). In this process, the diphenols corresponding to formula (I) are dissolved in aqueous alkaline phase. To prepare copolycarbonates with other diphenols, mixtures of diphenols corresponding to formula (I) and the other diphenols, for example those corresponding to formula (XI), are used. Chain terminators, for example corresponding to formula (XII), may be added to regulate molecular weight. The reaction is then carried out with phosgene by the interfacial condensation method in the presence of an inert, preferably polycarbonate-dissolving, organic phase. The reaction temperature is in the range from 0° to 40° C.

The branching agents optionally used (preferably 0.05 to 2 mol-%) may be initially introduced either with the diphenols in the aqueous alkaline phase or may be added in solution in the organic solvent before the phosgenation.

In addition to the diphenols of formula (I) and other diphenols (XI), mono- and/or bis-chlorocarbonic acid esters thereof may also be used, being added in solution in organic solvents. The quantity of chain terminators and branching agents used is then determined by the molar quantity of diphenolate structural units corresponding to formula (I) and, optionally, the other diphenols, for example those corresponding to formula (XI). Where chlorocarbonic acid esters are used, the quantity of phosgene may be reduced accordingly in known manner.

Suitable organic solvents for the chain terminators and, optionally, for the branching agents and the chlorocarbonic acid esters are, for example, methylene chloride, chlorobenzene, acetone, acetonitrile and mixtures of these solvents, particularly mixtures of methylene chloride and chlorobenzene. The chain terminators and branching agents used may optionally be dissolved in the same solvent.

The organic phase for the interfacial polycondensation may be formed, for example, by methylene chloride, chlorobenzene and by mixtures of methylene chloride and chlorobenzene.

Aqueous NaOH solution for example is used as the aqueous alkaline phase.

The production of the polycarbonates according to the invention by the interfacial process may be catalyzed in the usual way by such catalysts as tertiary amines, particularly tertiary aliphatic amines, such as tributylamine or triethylamine. The catalysts may be used in quantities of from 0.05 to 10 mol-%, based on mols diphenols used. The catalysts may be added before the beginning of phosgenation or during or even after phosgenation.

The polycarbonates according to the invention are isolated in known manner.

The high molecular weight, thermoplastic aromatic polycarbonates according to the invention may also be produced by the known homogeneous-phase process, the so-called "pyridine process" and also by the known melt transesterification process using diphenyl carbonate for example instead of phosgene. In this case, too, the polycarbonates according to the invention are isolated in known manner.

The polycarbonates obtainable by the process according to the invention preferably have molecular weights Mw (weight average, as determined by gel chromatography after preliminary calibration) of at least 9,000 and, more preferably, in the range from 12,000 to 190,000 and, most preferably, in the range from 19,000 to 65,000. They may be linear or branched and are homopolycarbonates or copolycarbonates based on the diphenols corresponding to formula (I).

Accordingly, the present invention also relates to high molecular weight, thermoplastic, aromatic polycarbonates having molecular weights Mw (weight average molecular weights) of at least 9,000 and, more preferably, in the range from 12,000 to 190,000 and, most preferably, in the range from 19,000 to 65,000 obtainable from the linear or branched diphenols of formula (I) by the process according to the invention.

Accordingly, the present invention also relates to high molecular weight, thermoplastic, aromatic polycarbonates having Mw values (weight average molecular weights) of at least 9,000, preferably in the range from 12,000 to 190,000 and more preferably in the range from 19,000 to 65,000 which contain bifunctional carbonate structural units corresponding to formula (Ia)

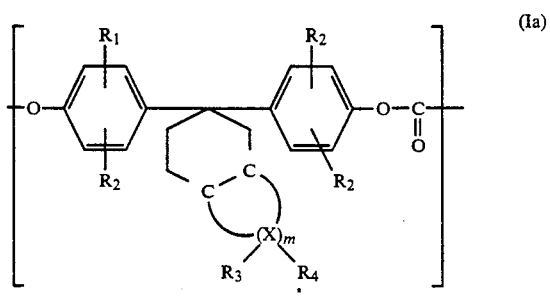

in which

X, $R_1$, $R_2$, $R_3$, $R_4$ and m are as defined for formula (I), in quantities of from 100 mol-% to 2 mol-%, preferably in quantities of from 100 mol-% to 5 mol-%, more preferably in quantities of from 100 mol-% to 10 mol-% and, most preferably, in quantities of from 100 mol-% to 20 mol-%, based in each case on the total quantity of 100 mol-% of difunctional carbonate structural units in the polycarbonate.

Accordingly, the polycarbonates according to the invention contain quantities—complementary in each case to 100 mol-%—of other difunctional carbonate structural units, for example those corresponding to formula (XIa)

in which —Z— is as defined for formula (XI), i.e. in quantities of of from 0 mol-% (inclusive) to 98 mol-% inclusive, preferably from 0 mol-% to 95 to mol-%, more preferably from 0 mol-% to 90 mol-% and most preferably from 0 mol-% to 80 mol-%, based in each case on the total quantity of 100 mol-% of difunctional carbonate structural units in the polycarbonate.

Polycarbonates based on cycloaliphatic bisphenols are basically known and are described, for example, in EP-O 164 476, DE-OS 20 63 052, FR 1 427 998, WP 80 00 348, BE 785 189. They frequently have relatively high glass transition temperatures, but other important physical properties, such as UV stability and heat ageing resistance are unsatisfactory.

It has surprisingly been found that, as already mentioned, it is possible to obtain new polycarbonates having favorable properties by incorporation of the diphenols of formula (I) according to the invention.

In addition, the properties of the polycarbonates may be varied with advantage through their combination with other diphenols, particularly with the diphenols corresponding to formula (XI).

The polycarbonates obtainable by the process according to the invention are isolated in known manner by separating off the organic phase obtained in the interfacial process, washing it until it is neutral and electrolyte-free and then isolating it in the form of granules, for example in an evaporation extruder, or by precipitation of the polycarbonates from organic solution and isolation.

The additives normally used for thermoplastic polycarbonates, such as stabilizers, mold release agents, pigments, flameproofing agents, antistatic agents, fillers and reinforcing materials may be added in the usual quantities to the polycarbonates according to the invention before or after their processing.

More particularly, it is possible to add, for example, carbon black, kieselguhr, kaolin, clays, $CaF_2$, $CaCO_3$, aluminium oxides, glass fibers and inorganic pigments both as fillers and as nucleating agents and, for example, glycerol stearates, pentaerythritol tetrasterate and trimethylol propane tristearate as mold release agents.

The polycarbonates according to the invention may be processed to moldings, for example by extruding the polycarbonates isolated in known manner to granules and processing the resulting granules in known manner by injection molding to form various articles, optionally after incorporation of the additives mentioned above.

The polycarbonates according to the invention may be used as moldings for any applications where hitherto known polycarbonates are used, i.e. in the electrical field and in the building field for covering and glazing purposes and in the domestic field.

In Examples B.1 and B.2 below, the relative viscosity is measured on 0.5% by weight solutions of the polycarbonate in $CH_2Cl_2$.

The glass temperature was measured by differential scanning calorimetry (DSC).

EXAMPLE B.1

18.90 g (0.05 mol) of the diphenol (II), 12.0 g (0.3 mol) NaOH and 182 ml water are dissolved while stirring in an inert gas atmosphere. A solution of 0.106 g (2.25 mol-%) phenol in 136 ml methylene chloride is then added. 9.9 g (0.100 mol) phosgene are introduced into the thoroughly stirred solution at pH 13 to 14 and at 21° to 25° C. 0.2 ml N-ethyl piperidine is then added, followed by stirring for 45 minutes. The bisphenolate-free aqueous phase is separated off, the organic phase is washed with water until neutral after acidification with phosphoric acid and is freed from the solvent. The polycarbonate has a relative solution viscosity of 1.148.

The glass temperature of the polymer was found to be 242° C. (DSC).

EXAMPLE B.2

10.92 g (0.03 mol) of the diphenol (II), 0.09 g (0.000775 mol) Na-phenolate and 27.67 g (0.3 mol).45% NaOH are dissolved in 285 ml water in an inert gas atmosphere. 123 ml methylene chloride are then added and 8 g (0.0809 mol) phosgene are introduced over a period of 9 minutes with stirring. After addition of 0.742 g (0.000655 mol) N-ethyl piperidine, the reaction mixture is stirred for another 30 minutes. The temperature during phosgenation and condensation was 25° C.; the pH value after the reaction was 13. The bisphenolate-free aqueous phase is separated off, the organic phase is washed with water until neutral after acidification with phosphoric acid and is freed from the solvent. The polycarbonate has a relative solution viscosity of 1.260.

The glass temperature of the polymer was found to be 240° C. (DSC).

What is claimed is:

1. In the process for the production of a high molecular weight, thermoplastic aromatic polycarbonate which comprises reacting at least one diphenol with at least one carbonate precursor, the improvement wherein at least one diphenol has the formula

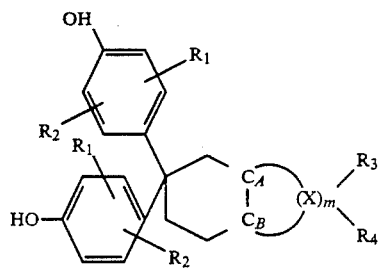

in which
$R_1$ and $R_2$ independently of one another represent hydrogen, halogen, $C_{1-8}$ alkyl, $C_{5-6}$ cycloalkyl, $C_{6-10}$ aryl or $C_{7-12}$ aralkyl,
m is an integer of from 3 to 7,
$R_3$ and $R_4$ are individually selected for each X and independently of one another represent, hydrogen, linear or branched $C_{1-6}$ alkyl, $C_{6-10}$ aryl or aralkyl, and
X represents carbon,
with the proviso that, at least one atom X, $R_3$ and $R_4$ are not both hydrogen, in a quantity of 100 mol-% to 2 mol-% based on the total mols of diphenols reacted.

2. The process of claim 1 wherein said carbonate precursor is phosgene.

3. The thermoplastic aromatic polycarbonate prepared by the process of claim 1 and having a weight average molecular weight of at least 9,000.

4. A thermoplastic aromatic polycarbonate having a weight average molecular weight of at least 9000 comprising bifunctional carbonate structural units corresponding to formula (Ia)

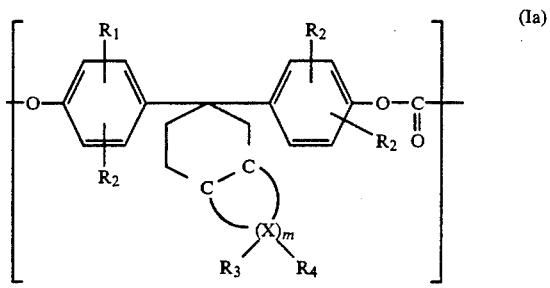

(Ia)

in which
$R_1$ and $R_2$ independently of one another represent hydrogen, halogen, $C_{1-8}$ alkyl, $C_{5-6}$ cycloalkyl, $C_{6-10}$ aryl or $C_{7-12}$ aralkyl,
m is an integer of from 3 to 7, $R_3$ and $R_4$ are individually selected for each X and, independently of one another represent hydrogen, linear or branched $C_{1-6}$ alkyl, $C_{6-10}$ aryl or aralkyl, and X represents carbon, with the proviso that, at at least one atom X, $R_3$ and $R_4$ are not both hydrogen, said structural units are present in quantities of 100 to 2 mol-%, relative to the total quantity of 100 mol-% of difunctional carbonate structural units in said polycarbonate.

* * * * *